United States Patent [19]

Wang et al.

[11] Patent Number: 5,144,030
[45] Date of Patent: Sep. 1, 1992

[54] FLUORESCENE POLARIZATION IMMUNOASSAY FOR TETRAHYDROCANNABINOIDS

[75] Inventors: Nai-Yi Wang, Mundelein; Robert E. Dubler, Gurnee; Frank S. Ungemach, Lake Villa; Roland L. Walters, Barrington; Susan A. Thacker, Naperville, all of Ill.

[73] Assignee: Abbott Laboratories, Abbott Park, Ill.

[21] Appl. No.: 366,266

[22] Filed: Jun. 12, 1989

Related U.S. Application Data

[63] Continuation-in-part of Ser. No. 14,950, Feb. 17, 1987, abandoned.

[51] Int. Cl.⁵ .................. C07D 491/16; C07D 311/80
[52] U.S. Cl. ..................... 546/89; 549/390; 549/391
[58] Field of Search ............... 549/390, 391, 324, 325; 546/89

[56] References Cited

U.S. PATENT DOCUMENTS

| | | | |
|---|---|---|---|
| 4,152,327 | 5/1979 | Zaugg et al. | 546/89 |
| 4,172,943 | 10/1979 | Zaugg et al. | 546/89 |
| 4,191,613 | 3/1980 | Ullman et al. | 435/188 |
| 4,205,952 | 6/1980 | Cais | 424/12 |
| 4,213,904 | 7/1980 | Haugland | 549/224 |
| 4,255,329 | 3/1981 | Ullman | 560/20 |
| 4,375,414 | 3/1983 | Strahilevitz et al. | 210/638 |
| 4,420,568 | 12/1983 | Wang et al. | 436/800 |
| 4,438,207 | 3/1984 | Fahrenholtz et al. | 436/543 |
| 4,476,229 | 10/1984 | Fino et al. | 436/800 |
| 4,620,977 | 11/1986 | Strahilevitz et al. | 424/85 |
| 4,721,787 | 1/1988 | Hutchison | 546/89 |

FOREIGN PATENT DOCUMENTS 0191640  8/1986  European Pat. Off. .

OTHER PUBLICATIONS

Pitt: J of the Amer. Chem. Soc. 97(13) p. 3798–3802, 1975.
Lander: Chemical Abstracts 84: 105813e (1976).
Apsimon: Chemical Abstracts 98: 16868y (1983).
Wilson: Chemical Abstracts 91: 49274k (1979).

*Primary Examiner*—C. Warren Ivy
*Assistant Examiner*—Raymond Covington
*Attorney, Agent, or Firm*—Thomas M. Breininger

[57] ABSTRACT

This disclosure related to a method and reagents for determining tetrahydrocannabinoids (THC) and THC metabolites in a biological fluid such as urine. In particular, this disclosure relates to a fluorescence polarization immunoassay procedure for determining the presence of THC and to a novel class of tracer compounds employed as reagents in such procedures. The procedure described also provides for novel wash reagent for a THC fluorescence polarization assay.

14 Claims, No Drawings

FLUORESCENE POLARIZATION IMMUNOASSAY FOR TETRAHYDROCANNABINOIDS

This application is a continuation-in-part of application Ser. No. 014,950, filed Feb. 17, 1987, entitled FLUORESCENCE POLARIZATION IMMUNOASSAY FOR TETRAHYDROCANNABINOIDS, by Nai-Yi Wang, et al., now abandoned.

TECHNICAL REVIEW

This invention relates generally to fluorescence polarization immunoassays and reagents useful therein, and particularly to such an assay for tetrahydrocannabinoids. Specifically tetrahydrocannabinoid tracers, immunogens and antibodies are disclosed as well as methods for making them.

BACKGROUND ART

Plants of the hemp family, specifically *Canabis sativa* produce significant amounts of cannabinoids. The most important cannabinoid is $\Delta^9$ tetrahydrocannabinol (THC) which produces the psychotrophic effects attributed to marijuana. The exact mechanism of action of THC is still unknown but its effects are primarily on the cardiovasular and central nervous systems.

The most common method for consumption of marijuana is by smoking. $\Delta^9$-THC is rapidly absorbed from the lungs into the blood stream. THC is rapidly metabolized through 11-hydroxy$\Delta^9$ THC to a series of polar metabolites with 11-nor-$\Delta^9$ THC-carboxylic acid being the primary metabolite. Approximately 80% of a dose of THC is eliminated during the first five days with 80% being excreted in the feces and the remainder in the urine. Depending upon assay sensitivity cannabinoid metabolites may continue to be detected in the urine for up to 10 days in occasional smokers and 36 days in chronic smokers.

In the past, cannabinoids have been detected in biological samples by thin layer chromatography, high pressure liquid chromatography (HPLC), gas chromatography (GC), gas chromatography/mass spectrometry (GC/MS), radioimmunoassay or enzyme immunoassay. However, these assay methods are not without drawbacks. Thin layer chromatography is labor intensive and lacks sensitivity. HPLC, GC, and GC/MS are labor intensive, requiring highly trained personnel to carry out extractions of the analyte from the biological matrix, while GC and GC/MS requires a derivatization step as well. Radioimmunoassay reagents degrade spontaneously, require burdensome methods of protecting and monitoring the safety of the personnel involved and generate hazardous waste which must be disposed of in a secure manner. Enzyme immunoassays are subjedct to variability due to thermal lability of reagents and to matrix effects which alter enzyme activity.

Fluorescence polarization immunoassay procedures provide a reliable quantitative means for measuring the amount of tracer-antibody complex produced in a homogeneous competitive binding assay. Typically, in such a competitive binding immunoassay a ligand (a substance of biological interest to be determined by the technique) competes with a labeled reagent, or "ligand analog," or "tracer" for a limited number of receptor binding sites on antibodies specific to the ligand and ligand analog. The concentration of ligand in the sample determines the amount of ligand analog which binds to the antibody: the amount of ligand analog that will bind is inversely proportional to the concentration of ligand in the sample, because the ligand and the ligand analog each bind to the antibody in proportion to their respective concentrations. Fluorescence polarization techniques are based on the principle that a fluorescent labeled compound, when excited by plane polarized light, will emit fluoresceence having a degree of polarization inversely related to its rate of rotation. Accordingly, when a tracer-antibody complex having a fluorescent label is excited with plane polarized light, the emitted light remains highly polarized because the fluorophore is constrained from rotating between the time that light is absorbed and emitted. In contrast, when an unbound tracer is excited by plane polarized light, its rotation is much faster than that of the corresponding tracer-antibody conjugate. As a result, the light emitted from the unbound tracer molecules is depolarized.

Such fluorescence polarization techniques have been applied in U.S. Pat. No. 4,420,568 to Wang, et al., which is directed to the use of a triazinylamino-fluorescent moiety as the fluorophore.

Cannabinoid antigen conjugates and antibodies have been described in U.S. Pat. No. 4,438,207 to K. Fahrenholt and J. Heveran, in U.S. Pat. No. 4,022,878 to S. Gross, in NIDA Research Monograph No. 7, 28 (1976) by Rowley et al., in NIDA Research Monograph No. 7, 15 (1976) by Cook et al., in Nature 249, 154 (1974) by Teale et al., in Nature New Biology 236, 216 (1972) by Grant et al. and in the Journal of Pharmacology and Pharmaceutics 27 465, (1975) by Teale et al.

The present invention is an advance in the art in that novel cannabinoid derivative compounds and novel reagents specifically useful in a fluorescence polarization assay are provided. An assay conducted in accordance with the present invention is particularly accurate, as will be explained infra.

SUMMARY OF THE INVENTION

The present invention relates to a method for determining tetrahydrocannabinoids ("THC") and THC metabolites, using fluorescence polarization techniques. Particularly, the present invention employs novel tracers of the formula:

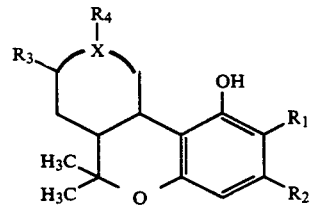

wherein:
R$_1$ is H when R$_2$ is n-pentyl, R$_3$ is H, R$_4$ is RZQ, and X is =C—, —C= or —CH; or R$_1$ is H when R$_2$ is n-pentyl, R$_3$ is RZQ, R$_4$ is CH$_3$ and X is =C—, —C= or —CH; or R$_1$ is RZQ when R$_2$ is n-pentyl, R$_3$ is H, R$_4$ is CH$_3$ or COOH, and X is =C—, or —C= or —CH; or R$_1$ is H when R$_2$ is —CH$_2$RZQ, R$_3$ is H, R$_4$ is CH$_3$ or COOH, and X is =C—, —C= or —CH; or R$_1$ is H when R$_2$ is R$_5$, R$_3$ is H, R$_4$ is H or RZQ, and X is —N—;

R$_5$ is an alkyl group of from about 5 to about 9 carbon atoms;

R is a linking group consisting of from about 0 to about 15 carbon atoms and heteroatoms, wherein said heteroatoms are N, O, S, Cl, Br, I or F;

Z is C=O, C=NH, NH, or SO$_2$; and

Q is fluorescein or a derivative of fluorescein, said fluorescein or derivative of fluorescein providing said tracer with the ability to emit fluorescence. (Formula I).

In preferred embodiments of the tracers, the fluorescein derivative is coupled to a linking group at the position R$_3$ through the functional group Z. Tracers having fluorescein coupled to a THC derivative by a R$_3$ linkage group exhibit surprisingly good span and intensity when used in fluorescence polarization techniques.

In addition, the present invention employs novel tracers of Formula I wherein ZQ is an imino, an iminocarbonyl, a carbonyl, a carbonimidoyl, an iminosulfonyl, a sulfonyl, an iminocarbonimidoyl, a thiocarbonyldiimino, an iminocarbonyloxy, an iminothiocarbonyloxy, a (sulfonyliminocarbonyl)diimino or a triazinyldiimino derivative of fluorescein, said derivative of fluorescein being linked to R by said imino, iminocarbonyl, carbonyl, carbonimidoyl, iminosulfonyl, sulfonyl, iminocarbonimidoyl, thiocarbonyldiimino, iminocarbonyloxy, iminothiocarbonyloxy, (sulfonyliminocarbonyl)diimino or triazinyldiimino group.

The present invention also provides a method for determining the presence or amount of tetrahydrocannabinoids and tetrahydrocannabinoid metabolites in a test sample of biological fluid by fluorescence polarization assay comprising the steps of:

(a) intermixing said test sample with a tracer of Formula I and an antibody capable of binding tetrahydrocannabinoids, or tetrahydrocannabinoid metabolites, and said tracer; and (b) determining the amount of tracer bound to said antibody by fluorescence polarization techniques as a measure of the amount of tetrahydrocannabinoids and tetrahydrocannabinoid metabolites in the sample.

For purposes of illustration only, the following tracer compounds may be employed in the novel methods of the present invention:

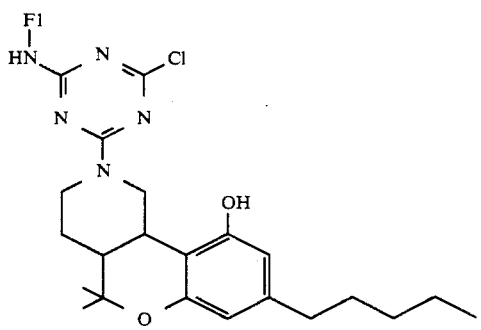

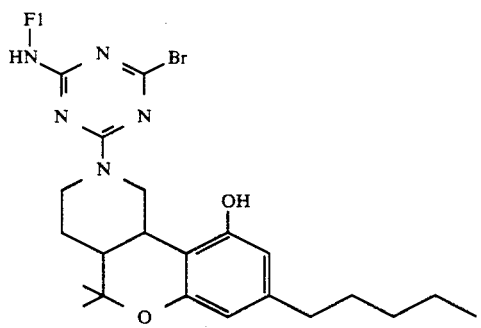

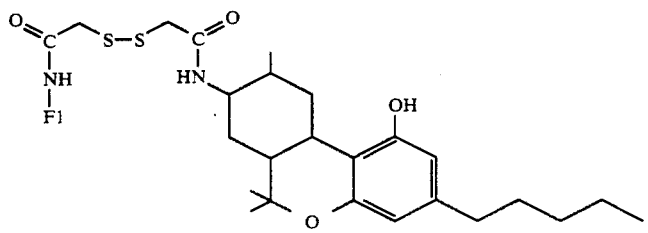

-continued
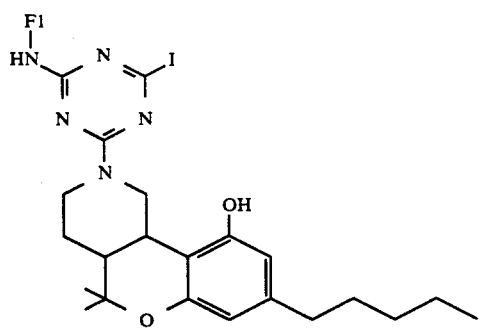
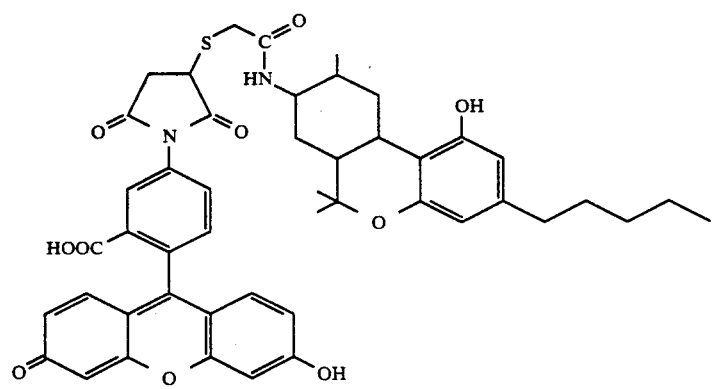
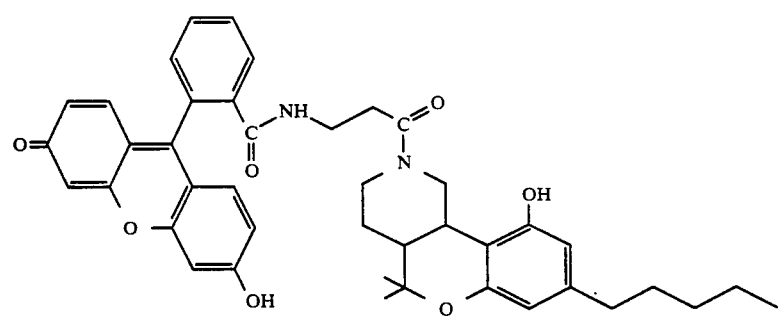
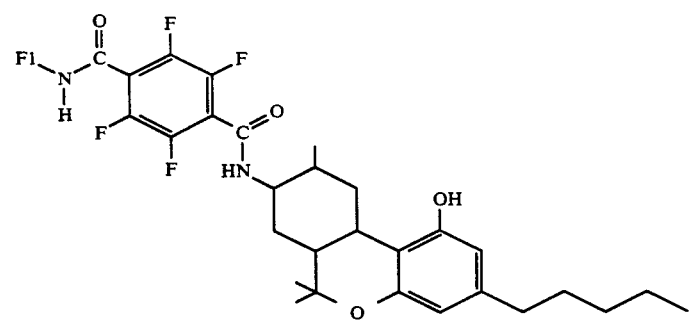
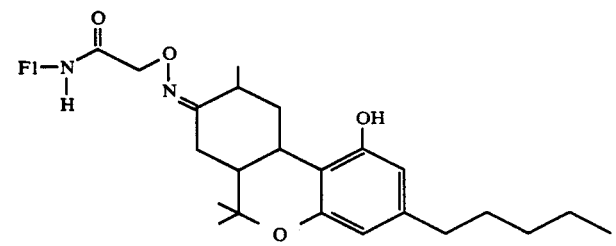

-continued

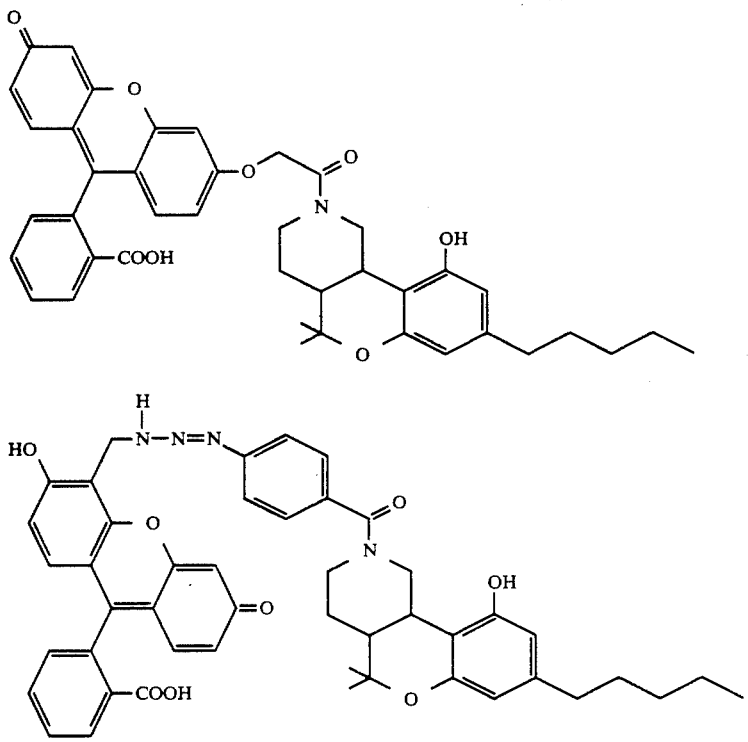

Antibodies useful in the present method are raised in response to immunogens made by chemically combining a compound of Formulae (I) wherein $R_1$ and $R_3$ are H, and X is =C— and when $R_4$ is R—Z—Q, $R_2$ is n-pentyl; when $R_2$ is R—Z—Q then $R_4$ is $CH_3$, $CH_2OH$ or COOH;

R is a linking group consisting of from about 0 to about 15 carbon atoms and heteroatoms, wherein said heteroatoms are N, O, S, Cl, Br, I or F;

Z is C=O, C=NH, $SO_2$, NH, $NCH_3$ or $CH_2$; and

Q is hydrogen, hydroxyl or a leaving group (with the proviso that when Z is $CH_2$; Q may not be hydrogen);

with a macromolecular or particulate carrier substance such as a poly(amino acid), a poly(amino acid) derivative or other macromolecular carrier or a synthetic polymeric bead bearing reactive functional groups on its surface.

In the case of automated fluorescence polarization assays utilizing automated dispensing means such as a pipette or probe, the present invention provides for a washing of the dispensing means with dimethylsulfoxide and sodium chloride solution to minimize sample carryover resulting from sample adhesion to the dispensing means. The preferred aqueous wash solution is about 50% dimethyl sulfoxide and 0.45% sodium chloride.

Thus, the present invention provides a method for determining the presence or amount of tetrahydrocannabinoids and tetrahydrocannabinoid metabolites in test samples of biological fluid by fluorescence polarization assay utilizing an automatic assay apparatus having a sample and reagent dispensing means comprising the steps of:

(a) intermixing said sample with a tracer of Formula I and an antibody capable of binding tetrahydrocannabinoids, or tetrahydrocannabinoid metabolites, and said tracer;

(b) determining the amount of said tracer bound to said antibody by fluorescence polarization techniques as a measure of the amount of tetrahydrocannabinoids and tetrahydrocannabinoid metabolites in the sample; and (c) washing said dispensing means in an about 50% dimethylsulfoxide and an about 0.45% sodium chloride aqueous solution.

Further, the invention relates to the elimination of potential fluorescence interference by riboflavin and other interfering substances. An amount of riboflavin binding protein (RBP) which would substantially reduce fluorescence interference by riboflavin is added either directly to each sample or to one or more of the reagents utilized in the assay, wherein it binds substantially all of the riboflavin which may be present in the sample into riboflavin binding protein-riboflavin complexes, thus substantially reducing or eliminating fluorescence interference by riboflavin. Other fluorescence-quenching substances (substances which reduce or eliminate fluorescing substances other than fluorescein, which potentially could increase the background of the assay and, thus, potentially increase the error in the assay results), such as sodium iodide, may also be utilized for this purpose.

Further objects and attendant advantages of the invention will be best understood from a reading of the following detailed description taken together with the drawings and the Examples.

DETAILED DESCRIPTION OF THE INVENTION

The term "ligand", as used herein, refers to a molecule, to which a binding protein, such as a receptor or an antibody, can be obtained or formed. The ligands of interest in the present invention are tetrahydrocannabinoids ("THC") and metabolites thereof. Generally ligands are protein-free compounds, of low molecular weight, which do not induce antibody formation when injected into an animal but which are reactive to antibodies. Ligands which are chemically modified for conjugation to a carrier protein are termed haptens. After the antibodies to haptens are raised, the resulting antibodies may be isolated by conventional, well-known antibody isolation techniques.

The term "ligand-analog", as used herein, refers to a mono-or polyvalent radical, a substantial portion of which has the same spatial and polar organization as the ligand to define one or more determinant or epitopic sites capable of competing with the ligand for the binding sites of a receptor. A characteristic of such a ligand-analog is that it possesses sufficient structural similarity to the ligand of interest as to be recognized by the antibody against the ligand. For the most part, the ligand-analog will have the same or substantially the same structure and charge distribution (spatial and polar organization) as the ligand(s) of interest (for purposes of the present invention, THC and metabolites) for a significant portion of the molecular surface. Frequently, the linking site for a hapten will be the same in preparing the antigen for production of antibodies as that used in the tracer for linking to the ligand, the same portion of the ligand analog which provides the template for the antibody will be exposed by the ligand analog in the tracer.

The present invention involves the use of fluorescein and derivatives of fluorescein. In particular, a necessary property of fluorescein and its derivatives for the usefulness of the tracer compounds is the fluorescence of fluorescein. Fluorescein exists in the two tautomeric forms shown below (II), depending on the acid concentration (pH) of the environment.

forms, if they exist for a particular molecule, except in the context of fluorescence. An open form is necessary for the fluorescence to occur.

The numbering of carbon atoms of the fluorescein molecule varies, depending upon whether the open or closed form of the molecule is considered. Accordingly, the literature concerning fluorescein and its compounds is not uniform as to carbon atom numbering. In the closed form, the para-carbon to the caronyl of the lactone on the phenyl ring is number "6". In the open form, the para-carbon to the carboxylic acid group on the phenyl ring is numbered "5". In this disclosure the numbering of the closed form is adopted because the raw materials used in the syntheses are most popularly numbered with that system. The carbon atom of fluorescein and its compounds which is opposite the carboxyl group is therefore numbered "6" for the purposes of the present disclosure.

A tracer in solution which is not complexed to an antibody is free to rotate in less than the time required for absorption and re-emission of fluorescent light. As a result, the re-emitted light is relatively randomly oriented so that the fluorescence polarization of a tracer not complexed to an antibody is low, approaching zero. Upon complexing with a specific antibody, the tracer-antibody complex thus formed assumes the rotation of the antibody molecule which is slower than that of the relatively small tracer molecule, thereby increasing the polarization observed. Therefore, when a ligand competes with the tracer for antibody sites, the observed polarization of fluorescence of the resulting mixture of the free tracer and tracer-antibody complex assumes a value intermediate between that of the tracer and that of the tracer-antibody complex. If a sample contains a high concentration of the ligand, the observed polarization

II

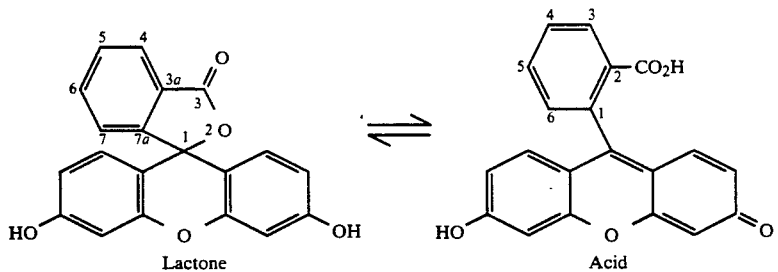

Lactone        Acid

In the open (acid) form, there are a number of conjugated double bonds which make that form of fluorescein (and compounds containing a fluorescein moiety) capable of absorbing blue light and emitting green fluorescence after an excited state lifetime of about four nanoseconds. When the open and closed forms coexist, the relative concentration of molecules in the open and closed forms is easily altered by adjustment of the pH level. Generally, the tracer compounds of the present invention exist in solution as biologically acceptable salts such as sodium, potassium, ammonium and the like, which allows the compounds to exist in the open, fluorescent form, when employed in the analytical methods of the present invention. The specific salt present will depend on the buffer employed to adjust the pH level. For example, in the presence of a sodium phosphate buffer, the compounds of the present invention will generally exist in the open form, as a sodium salt.

As used herein, the term "fluorescein," either as an individual compound or as a component of a larger compound, is meant to include both the open and closed value is closer to that of the free ligand, i.e., low. If the test sample contains a low concentration of the ligand, the polarization value is close to that of the bound ligand, i.e., high. By sequentially exciting the reaction mixture of an immunoassay with vertically and then horizontally polarized light and analyzing only the vertically polarized component of the emitted light, the polarization of fluorescence in the reaction mixture may be accurately determined. The precise relationship between polarization and concentration of the ligand to be determined is established by measuring the polarization values of calibrators with known concentrations. The concentration of the ligand can be interpolated from a standard curve prepared in this manner.

The particular antibodies and tracers formed in accordance with this invention have been found to produce very good assays, as discussed infra.

THE REAGENTS

The objective in designing a Fluorescence Polarization Immunoassay for THC and THC metabolites is to have competition between THC and THC metabolites and the tracer for the recognition sites of the antibody. Great variations in the structure of the haptens and tracers are allowed in achieving this goal. For purposes of this invention, "haptens" are precursors of the immunogens or tracers, comprising generally a substituted THC derivative and a linking group to the protein carrier or fluorescein compound.

THE TRACERS

(a) The Structure of the Tracers

The tracers of the present invention have the general structural formula I, where Q represents a fluorescein moiety or a fluorescein derivative. Alternatively the tracers can have the structure:

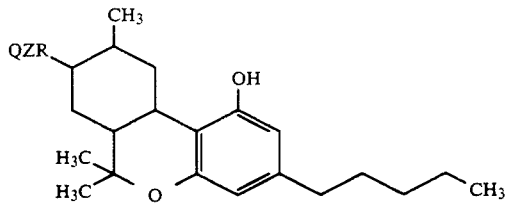

wherein Z is a linking group such as described below. For example, ZQ may be an imino, an iminocarbonyl, a carbonyl, a carbonimidoyl, an iminosulfonyl, a sulfonyl, an iminocarbonimidoyl, a thiocarbonyldiimino, an iminocarbonyloxy, an iminothiocarbonyloxy, a (sulfonyliminocarbonyl)diimino or a triazinyldiimino derivative of fluorescein, said derivative of fluorescein being linked to R by said imino, an iminocarbonyl, carbonyl, carbonimidoyl, iminosulfonyl, sulfonyl, iminocarbonimidoyl, thiocarbonyldiimino, iminocarbonyloxy, iminothiocarbonyloxy, (sulfonyliminocarbonyl)diimino or a triazinyldiimino group. Most preferably, the tracers have the following structure:

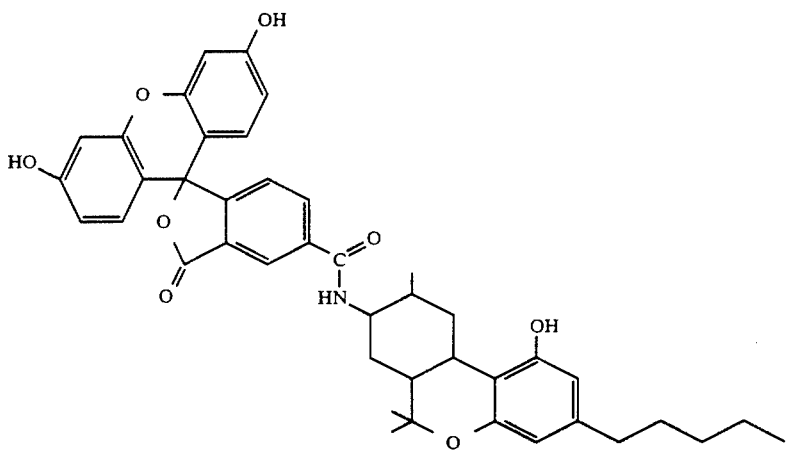

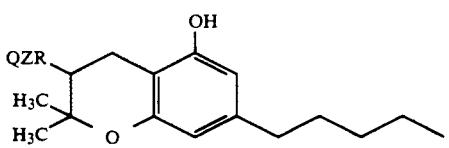

wherein Q, Z and R are as defined previously. For example, ZQ may be an imino, an iminocarbonyl, a carbonyl, a carbonimidoyl, an iminosulfonyl, a sulfonyl, an iminocarbonimidoyl, a thiocarbonyldiimino, an iminocarbonyloxy, an iminothiocarbonyloxy, a (sulfonyliminocarbonyl)diimino or a triazinyldiimino derivative of fluorescein, said derivative of fluorescein being linked to R by said imino, iminocarbonyl, carbonyl, carbonimidoyl, iminosulfonyl, sulfonyl, iminocarbonimidoyl, thiocarbonyldiimino, iminocarbonyloxy, iminothiocarbonyloxy, (sulfonyliminocarbonyl)diimino or triazinyldiimino group. When R is NH, Z is C=O and Q is fluorescein or a derivative of fluorescein, ZQ may be an iminocarbonyl or a carbonyl derivative of fluorescein, said derivative of fluorescein being linked to R by said iminocarbonyl or carbonyl group.

In a preferred form of the invention, the tracers have the following structure:

The tracer is a THC derivative that is linked to a fluorescein derivative by, for example, an amido, amidino, triazinylamino, carbamido, thiocarbamido, carbamoyl, thiocrbamoyl, or sulfonylcarbamoyl group. The tracers are prepared by linking the appropriate fluorescein derivative to a THC derivative containing an amino, carboxylic acid, sulfonic acid, mercapto, hydroxy, imidate, hydrazide, isocyanate, thioisocyanate, chloroformate, chlorothioformate, chlorosulfonylcarbamoyl, or the like group, as will be discussed in the context of the synthetic method and the Examples below.

By way of example, any of the following fluorescein derivatives can be used:

| | |
|---|---|
| Fl-NH₂ | fluorescein amine |
| Fl-CO₂H | carboxyfluorescein |
| Fl-NHCOCH₂I | 2-iodoacetamidofluorescein |
| Fl-NHCOCH₂Br | 2-bromoacetamidofluorescein |

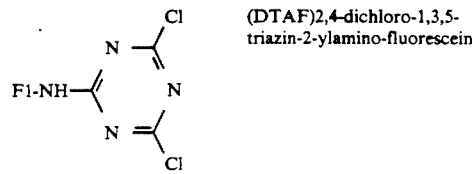 (DTAF)2,4-dichloro-1,3,5-triazin-2-ylamino-fluorescein

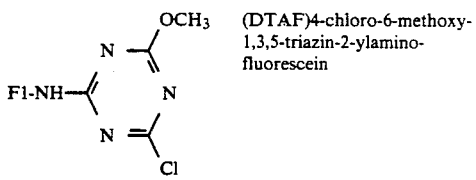

| | |
|---|---|
| Fl-NCS | fluorescein thioisocyanate |
| Fl-CH$_2$NH$_2$ | 11-aminomethylfluorescein |

For purposes of illustration only, a novel tracer of the present invention may be a tracer of Formula I wherein ZQ is an aminotriazinylamino derivative of fluorescein, 4-chloro-6-(fluorescein-6-ylamino)-1,3,5-triazin-2-ylamino, fluorescein-5-ylcarbonyl, fluorescein-6-ylcarbonyl, fluorescein-5-ylamino or fluorescein-6-ylamino.

b. The Synthesis of the Tracers

The tracers of the present invention are made by coupling a fluorescein moiety, or a derivative of fluorescein, to the general structure shown in Formula I. The fluorescein moiety can be linked to the amino, carboxyl, imidate or alkoxy functional group by an amide, an amidine, an urea, a thiourea, a carbamate, a thiocarbamate, triazinylamino, or sulfonylcarbamate linkage. In the presently preferred embodiment, the fluorescein derivative is carboxy fluorescein(vi) and this is coupled to a precursor such as

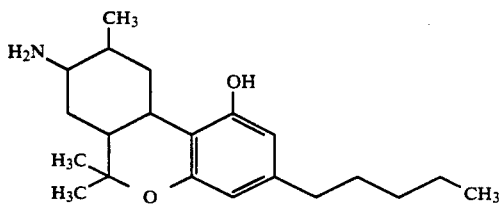

6aR-Trans-1-(hydroxy)-8-amino-6a,7,8,10,10a-hexahydro-6,6,9-trimethyl-3-pentyl-6H-dibenzo (b,d) pyran.

All THC derivatives that have a terminal amino group, such as amino, hydrazinyl, hydrazido or the like, are coupled to carboxyfluorescein by the active ester method or the mixed anhydride method, and coupled to fluorescein isothiocyanate, DTAF or alkoxy DTAF by simply mixing the two materials in solution. The amino group can be converted to the isocyanate and thioisocyanate groups by reaction with phosgene and thiophosgene, respectively. These are then condensed with aminofluorescein to produce the tracer.

All THC derivatives that have a terminal carboxylic acid group, such as carboxylic acid, (aminohydroxy)alkylcarboxylic acid or the like, are coupled to aminofluorescein and aminoethylfluorescein by the active ester method.

All THC derivatives that have a terminal hydroxy group can be coupled to fluorescein by reaction with DTAF, α-iodoacetamidofluorescein, α-bromoacetamido fluorescein or fluorescein isothiocyanate.

THC derivatives that have a terminal nitrile group can be prepared from halides or sulfonate esters. They are converted to imidates in anhydrous alcohol in the presence of hydrogen chloride gas. The imidate is then coupled to fluorescein amine in solution to prepare the tracer.

Preparation of the various amino, hydroxy and mercapto derivatives of the THC derivatives is described herein in the immunogen preparation section.

The preferred tracers are prepared in five steps from the acetate having the structural formula:

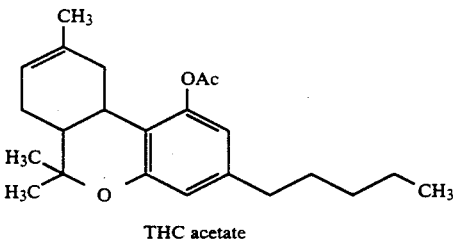

THC acetate

Epoxidation of the double bond with 3-chloro perbenzoic acid gives the following epoxide:

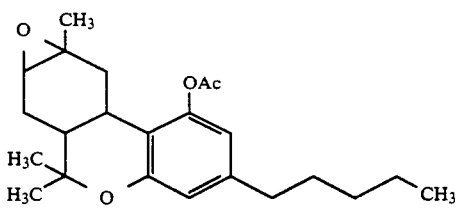

6aR-Trans-1-(acetyloxy)-6a,7,8,9,10,10a-hexahydro-6,6,9-trimethyl-3-pentyl-6H-dibenzo(b,d)pyrano(8,9-b)oxirene which is rearranged to the α-methylketone of the following structure:

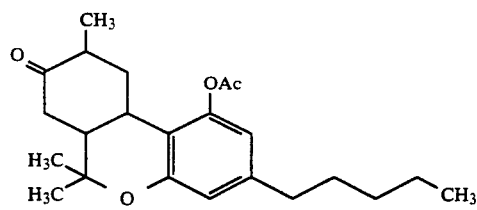

6aR-Trans-1-(acetyloxy)-6a,7,8,9,10,10a-hexahydro-6,6,9-trimethyl-8-oxo-3-pentyl-6H-dibenzo(b,d)pyran on treatment with boron trifloride etherate. The amino group is introduced by reductive amination. After the removal of the acetate protecting group, the primary amine, chemical structure V, is coupled to fluorescein carboxylic acids.

THE ANTIBODIES

The antibodies of the present invention are prepared by eliciting a response to the immunogens described herein. The immunogen is administered to animals or to in vitro cultures of immunocompetent cells by a series of inoculations, in a manner well known to those skilled in the art.

Usable antibodies can be produced from a variety of THC derivatives. Referring to formula 1, immunogens prepared from compounds functionalized either at the 2,5' or 9 position can produce antibodies in animals; such antibodies are useful in a THC and THC metabolites assay according to the invention when combined with the appropriate tracers.

a. The Structure of the Immungens

The immunogens of the present invention have the general structural formula shown in Formula (I) as defined for immunogens herein. The immunogens can be prepared by coupling a compound of the class shown in Formula (I) with a poly(amino acid) or a derivative of a poly(amino acid) or other immunologically active carrier as will be discussed in the context of the synthetic method and the Examples below.

In a preferred form of the immunogen substitutuion of the C-9 position is preferred from a structural point of view, the availability of starting material and the simplicity of the chemical synthesis, and the greater probability of obtaining useful antisera from a given animal. Accordingly, the preferred embodiment of this aspect of the invention comprises 9-position derivatives represented by the general structural formula (I) (where R, $R_1$, $R_2$, $R_3$ and $R_4$, are as defined in the summary of the invention, Z is C=O, C—NH, $SO_2$, NH, $NCH_3$ or $CH_2$ and Q is the immunogenic carrier). In the most preferred form of this aspect of the invention, the immunogens are represented by the structural formula:

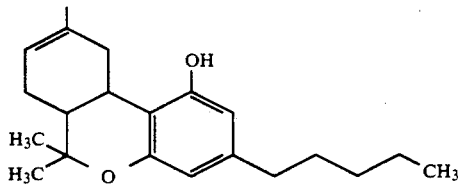

IX

The structure is preferred because it provides antisera with sensitivity to a broad range of THC and THC metabolites while excluding other drugs and endogenous substances.

Although bovine thyroglobulin is the poly(amino acid) in this most preferred form, it should be understood that various protein carriers can be employed, including albumins, serum proteins, globulins, ocular lens proteins, lipoproteins and the like. Illustiative protein carriers include bovine serum albumin, keyhole limpet hemocyanin, egg ovalbumin, bovine gamma globulin, thyroglobulin, etc. Alternatively, synthetic poly(amino acids) having a sufficient number of available amino groups such as those on lysine or ornithine residues can be employed, as can many other synthetic or natural polymeric materials bearing reactive functional groups. In addition, carbohydrates, yeasts, polysaccharides or any other substance that can be used as an immunological carrier can be conjugated to the hpaten to produce an immunogen.

For example, a novel immunogen of the present invention may have the following structure:

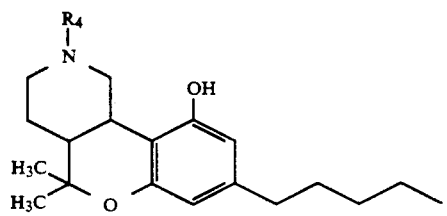

XIII wherein:
$R_4$ is RZQ;

R is a linking group consisting of from about 0 to about 15 carbon atoms and heteroatoms, wherein said heteroatoms are N, O, S, Cl, Br, I or F;

Z is C=O, C=NH, $SO_2$, NH, $NCH_3$ or $CH_2$; and

Q is a poly(amino acid), a poly(amino acid) derivative, or another immunologically active carrier. Thus, for purposes of illustration only, RZ may be an amide, an amidine, an alkyl, a urea, a thiourea, a carbamate, or a thiocarbamate linkage.

b. The Synthesis of the Immunogens

The immunogens of the present invention are made by coupling a hapten, such as that shown by the general structure of formula (I) to a poly(amino acid). The poly(amino acid) can be linked to the hapten by an amide, an amidine, an alkyl, a urea, a thioura, a carbamate, or a thiocarbamate linkage. In a preferred embodiment, the poly(amino acid) coupled to hapten is bovine thyroglobulin. The hapten is preferably coupled under conditions normally used to form amide linkages; which conditions are well known to those skilled in the art. The immunoges are prepared by coupling a hapten that contains an —$NH_2$, —$CO_2H$, —$CONHNH_2$, —CNOR, —CHO, —Br, —I, —NCO, —NCS, —OCOCl, —$SO_2Cl$ or OCSCl group to a poly(amino acid). Haptens containing an $NH_2$ group can be coupled by activating the carboxylic acid group on the poly(amino acid) in the presence of the —$NH_2$ group. For aromatic amines, the diazonium salt method can be used. The diazonium salt, prepared by mixing the amine with sodium nitrite in acid solution, is added to the poly(amino acid). Activation of the carboxylic acid groups on the poly(amino acid) can be accomplished by mixing the hapten and the poly(amino acid) with 1-ethyl-3-(3-dimethylaminopropyl) carbodiimide (EDC), N,N'-dicyclohexylcarbodiimide (DCC), 1-cyclohexyl-3-(2-morpholinoethyl) carbodiimide methoxy-p-toluenesulfonate, or the like. Carboxylic acid-containing haptens are also coupled by the in situ activation method (EDC) or the active ester method, as described previously in the tracer synthesis section. For —$CONHNH_2$, coupling is performed as for a non-aromatic amino group. A —CNOR compound, which is prepared from the corresponding cyano compound, is coupled directly to the poly(amino acid). A —CHO compound is coupled to the poly(amino acid) by reductive amination. The poly(amino acid) is mixed with the —CHO hapten and the resulting imine is reduced with a borohydride reducing agent such as sodium cyanoborohydride to yield alkylated amines of the poly(amino acid). Isocyanate (—NCO) and isothiocyanate (—NSC) compounds, which are prepared from the corresponding amino compound, and chloroformate (—OCOCl) and chlorothioformate (—OCCl) compounds, which are prepared from the corresponding alcohol compound, produce urea, thiourea, carbamate and thiocarbamate linkages, respectively. This is accomplished by directly coupling the hapten to the poly(amino acid).

The syntheses of the above haptens (immunogen precursors) are accomplished is very similar ways. Formula X below shows an immunogen precursor class in accordance with a preferred embodiment of the method of the present invention.

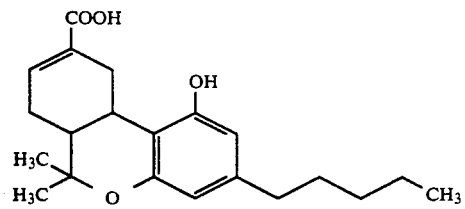

In general, the 9-substituted haptens are preapred by protection of the phenol moiety of $\Delta^8$-THC followed by allylic oxidation of the C-9 methyl group using selenium dioxide. The resulting allylic alcohol is then oxidized to the aldehyde by pyridinium chlorochromate. Reductive animation of the aldehyde gives a primary amine which is coupled to the poly(amino acid) or other carrier.

For longer chain haptens, the aldehyde can be condensed with (aminohydroxy) alkylcarboxylic acids, such as $NH_2OCH_2CO_2H$, to produce substituted oxime derivatives. The oxime alkylcarboxylic acid derivatives can be partially reduced to the corresponding (aminohydroxy) alkylcarboxylic acid derivatives. Finally the protecting group is removed and the compound is coupled to the poly(amino) acid or other carrier.

Alternatively, the aldehyde can be further oxidized to the corresponding carboxylic acid with sodium chlorite in the presence of a phosphate buffer and a halogen scavenger. The phenol-protected carboxylic acid can be coupled to $\Omega$ diamines to generate terminal amino groups which, after deprotection are linked to poly(amino) acid through the amide bonds.

Aldehydes or ketones can be derivatized by known methods to a variety of compounds containing a suitable group useful for coupling to a carrier protein, such as, Wittig reaction, condensation with hydrazine compounds, reductive amination with amino compounds or the like.

Nitrile derivatives can be converted to alkoxy imidates by treating the nitrile with anhydrous alcohol and hydrogen chloride gas. The hydrazide derivatives can be prepared from the corresponding carboxylic acid derivatives by active ester coupling with hydrazine or by reacting hydrazine with the corresponding carboxylic ester derivative. Amines are convertible to the isocyanate or thioisocyanate derivatives and alcohols are convertible to chloroformate and chlorothioformate derivatives by reaction of the amine or the alcohol with phosgene or thiophosgene.

3. Wash Reagent

It has been determined that providing a THC fluorescence assay with an aqueous/organic wash reagent improves assay reliability and accuracy. Specifically, it has been found that providing a wash solution with about 20% DMSO to about 80% DMSO, most preferably 50% dimethylsulfoxide and about 0.45% NaCl to about 0.9% NaCl, most preferably about 0.45% sodium chloride in an aqueous solution eliminates $\Delta^9$-THC metabolite adhesion to dispensing means such as a probe, pipette, or syringe. It is to be understood that urine adhesion to the dispensing means can result in sample contamination yielding false positive results for samples tested subsequent to a THC-containing sample. In the case of highly automated assaying apparatus, such as the ABBOTT TDx®, which tests large numbers of samples sequentially, eliminating urine "carry-over" between samples is highly desirable.

In accordance with the analytical methods of the present invention, i.e., the methods of detecting cannabinoid by a fluorescence immunoassay procedure using the tracer and antibody compounds of the invention, a sample containing or suspected of contaiing a $\Delta^9$-tetrahydrocannabinol or metabolite is intermixed with a biologically acceptable salt of a tracer and an antibody specific to cannabinoids and to the tracer. The cannabinoid metabolite and tracer compete for a limited number of antibody sites, resulting in the formation of complexes. Because the concentration of tracer and antibody is maintained constant, the ratio of cannabinoid-antibody complex to tracer-antibody complex formed is directly proportional to the amount of cannabinoid in the sample. Therefore, upon exciting the mixture with linearly polarized light and measuring the polarization of the fluorescence emitted by a tracer and a tracer-antibody complex, one is able to determine qualitatively whether or not cannabinoids are present in the sample.

The results can be quantified in terms of net millipolarization units, span (in millipolarization units) and relatively intensity. The measurement of millipolarization units indicates the maximum polarization when a maximum amount of the tracer is bound to the antibody in the absence of any cannabinoid. The higher the net millipolarization units, the better the binding of the tracer to the antibody. The span is an indication of the difference between the net millipolarization at the points of maximum and minimum amount of tracer bound to the antibody. A larger span provides for a better numerical analysis of data. The intensity is a measure of the strength of the signal above background. Thus, a higher intensity will give a more accurate measurement. The intensity is determined at about 0.5 to 2.0 nanomolar for the preferred tracers of the invention, as the sum of the vertically polarized intensity plus twice the horizontally polarized intensity. The intensity of the tracer signal can range from about five times to about fifty times the background noise, depending upon the concentration of the tracer and other assay variables. For the purposes of the present invention, an intensity of at least five times that of background noise is preferred.

Table I-IV shows the result obtained with various embodiments of the present invention, in terms of span, millipolarization units and intensity. In all Tables I-IV, the antiserum employed was raised in sheep. As can be seen from this data, an assay produced by use of the tracer of Formula IV provides excellent results and is presently the most preferred. In addition, the tracers represent by Formulas XI and XII below, also produced acceptable results and thus are alternative preferred tracers. With respect to Formula XIII, ZQ may be an imino, an iminocarbonyl, an iminosulfonyl, a thiocarbonyldiimino, or a (sulfonyliminocarbonyll-)diimino derivative of fluorescein, said derivative of fluorescein being linked to R by said limino, iminocarbonyl, iminosulfonyl, thiocarbonyldiimino or (sulofonyliminocarbonyl)diimino group.

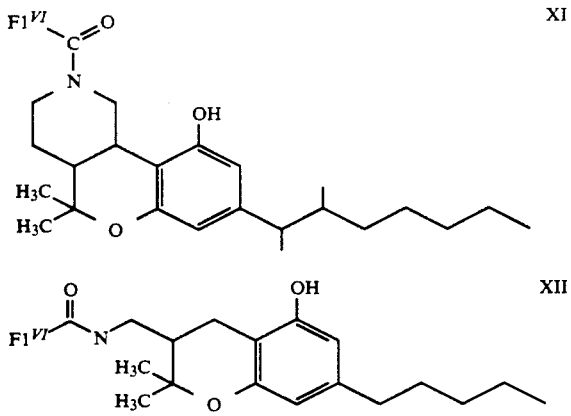

TABLE I

| Tracer | Sheep 126 Net Polarization | Span | Intensity |
| --- | --- | --- | --- |
| Formula XII | 173 | 14 | 15.0 |
| Formula IV | 141 | 70 | 11.7 |

TABLE II

| Tracer | Sheep 130 Net Polarization | Span | Intensity |
| --- | --- | --- | --- |
| Formula XII | 178 | 13 | 15.3 |

TABLE III

| Tracer | Sheep 128 Net Polarization | Span | Intensity |
| --- | --- | --- | --- |
| Formula IV | 119 | 58 | 11.1 |

TABLE IV

| Tracer | Sheep 127 Net Polarization | Span | Intensity |
| --- | --- | --- | --- |
| Formula IV | 220 | 24 | 11.7 |
| Formula XI | 99 | 13 | 13.6 |

The pH at which the method of the present invention is practiced must be sufficient to allow the fluorescein moiety of the tracers to exist in their open form. The pH may range from about 3 to 12, more preferably in the range of from about 5 to 10, and most desirably from about 6 to 9. Various buffers may be used to achieve and maintain the pH during the assay procedure. Representative buffers include borate, citrate, acetate, phosphate, carbonate, tris, barbital and the like. The particular buffer employed is not critical to the present invention, but the tris and phosphate buffers are preferred. The cation portion of the buffer will generally determine the cation portion of the tracer salt in solution.

The preferred method of the improved assay of the present invention is discussed in detail in Example 5. The assay is a "homogeneous assay", which means that the end polarzation readings are taken from a solution in which bound tracer is not separated from unbound tracer. This represents a distinct advantage over heterogeneous immunoassay procedures wherein the bound tracer must be separated from the unbound tracer before a reading can be taken.

The reagents for the fluorescence polarization assay of the present invention comprise antibody selective for $\Delta^9$-tetrahydrocannabionol and its metabolites and tracer. Additionally, largely conventional solutions including a cannabinoid-specific pretreatment solution, a dilution buffer, cannabinoid calibrators and cannabinoid controls are desirably prepared. Typical solutions of these reagents, some of which are described herein, are commercially available in assay "kits" from Abbott Laboratories, Abbott Park, Ill.

The preferred procedure is especially designed to be used in conjunction with the Abbott Laboratories' $TD_x$ ® Clinical Analyzer available from Abbott Laboratories, Irving, Tex. It is to be understood that when the Abbott Laboratories $TD_x$ ® Clinical Analyzer is used, the assay is fully automated from pretreatment to final reading. However, a manual assay can be performed. In the case of automated and manual assays, the sample is mixed with the pretreatment solution in dilution buffer and a background reading is taken. The tracer is then mixed with the assay. The antibody is then finally mixed into the test solution. After incubation, a fluorescence polarization reading is taken and processed.

It should be understood that the foregoing Detailed Description and the following Examples are intended to illustrative and not limiting, with respect to the scope of the present invention. Various modifications will become apparent to one skilled in the art, and thus it is intended that the scope of the invention be defined solely by the claims and legal equivalents thereof.

EXAMPLE 1—Preparation of Immunogens (a) Hapten Preparation

6aR-trans-1-(acetyloxy)-6a,7,10,10a-tetrahydro-6,6,9-trimethyl-3-pentyl-6H-dibenzo [b,d] pyran A mixture of 6aR-trans-6a,7,10,10a-tetra-hydro-6,6,9-trimethyl-3-pentyl-6H-dibenzo [b,d] pyran-1-ol ($\Delta^8$-THC) (1 g, 3.18 mmol) acetic anhydride (9 ml), and pyridine (13 ml) was stirred at room temperature for 16 hours. The volatiles were removed by evaporation in vacuo to give 1.05 g of crude product.

6-aR-trans-1-(acetyloxy)-6a,7,10,10a-tetrahydro-6,6-dimethyl-3-pentyl-6H-dibenzo-[b,d]pyran-9-methanol To a solution of the crude acetate obtained above (1.05 g) in absolute ethanol (18 ml) was added selenium dioxide (650 mg, 5.86 mmol). The resulting mixture was heated at reflux for 7 hours under nitrogen with stirring. After cooling to room temperature, the black precipitate was removed by filtration and the filtrate was rotary-evaporated to give a crude product which was flash-chromatographed over silica gel (125 ml). Elution with hexane/ethyl acetate (2:1) afforded 230 mg of a viscous liquid. (two-step from $\Delta^8$-THC, 20% yield).

6aR-trans-1-(acetyloxy)-6a,7,10,10a-tetrahydro-6,6-dimethyl-3-pentyl-6H-dibenzo-[b,d]pyran-9-carboxaldehyde To a stirred mixture of the allylic alcohol obtained above (230 mg, 0.62 mmol), sodium acetate (23 mg, 0.28 mmol) and methylene chloride (11 ml), was added pyridinium chlorochromate (PCC, 230 mg, 1.07 mmol). After stirring at room temperature for 2 hours, the mixture was diluted with ether (50 ml) and stirring was continued for 10 minutes. The suspension was then filtered through a short column of silica gel (60 ml, Merck 60-200 mesh). The column was washed with additional portions of ether until the washings were negative by UV test. The eluents were combined and rotary-evaporated to give 220 mg (96% yield) of the desired aldehyde.

6aR-trans-1-(acetyloxy)-6a,7,10,10a-tetrahydro-6,6-dimethyl-3-pentyl-6H-dibenzo-[b,d]pyran-9-caroxylic acid To a mixture of the aldehyde prepared above (168 mg, 0.45 mmol) 2-methyl-2-butene (0.38 ml), and tert-butanol (15 ml) was added a solution of sodium chlorite (366 mg, 4.95 mmol) and sodium dihydrogen phosphate monohydrate (366 mg, 2.89 mmol) in water (3 ml). The mixture was stirred at room temperature for 16 hours. After removal of the volatiles in vacuo, the residue was partitioned between ether and water (3 times). The ether layers were combined, washed with brine, and dried (magnesium sulfate) to give 176 mg (100% yield) of an oil.

6aR-trans-1-(acetyloxy)-6a,7,10,10a-tetrahydro-1-hydroxy-6,6-dimethyl-3-pentyl-6H-dibenzo-[b,d]pyran-9-carboxylic acid The mixture of the carboxylic acid described above (209 mg, 0.54 mmol) anhydrous potassium carbonate (316 mg, 2.28 mmol), and methanol (12 ml) was stirred at room temperature for 16 hours. Water was added and the aqueous solution was acidified with dilute hydrochloric acid (to pH 3). The liberated acid was then extracted with ethyl acetate (3 times) and the combined extracts were washed with brine and dried (sodium sulfate). Rotary evaporation of the solution, followed by further drying in vacuo, gave 190 mg of a crude product.

(b) Immunogen Prepartation

Hapten

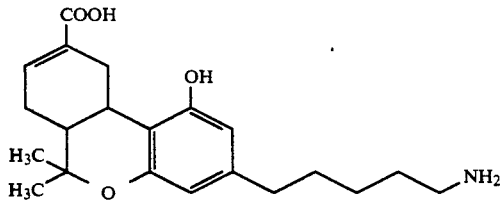

Twenty-four milligrams of 5' amino-11-nor-$\Delta^8$-tetrahyderocannabinol-9-carboxylic acid was dissolved in 4 ml of 50% DMSO-water (v/v). This was added to a rapidly stirring solution of 50% DMSO-water containing 66 milligrams of glutaraldehyde activated bovine serum albumin. The mixture was stirred for 18 hours at 4° C. after which it was dialyzed against phosphate buffer to remove unbound hapten.

Hapten

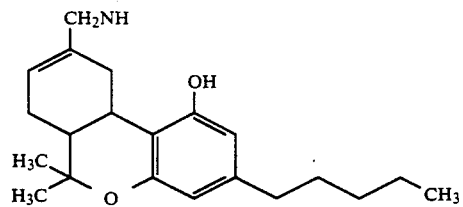

Thirty-seven milligrams of 11-amino-$\Delta^8$-tetrahydrocannabinol was dissolved in 0.5 ml of methanol. The methanol solution was added to a rapidly stirring solution of 50% DMSO/water (v/v) containing 33 mg of glutaraldehyde activated bovine serum albumin. This mixture was stirred for 18 hours at room temperature and then dialyzed against phosphate buffer to remove unbound hapten.

Immunogen of Figure X

Dissolve 29.5 mg of 11-nor-$\Delta^8$-tetrahydrocannabinol-9-carboxylic acid in 1.0 ml of DMSO. While stirring, add 17.2 mg of N-hydroxysuccinimide and 32 mg of dicyclohexyl-carbodiimide and react at room temperature for 90 minutes. Remove precipitate by filtration and add the filtrate to a rapidly stirring solution of 60% DMSO-water (v/v) containing 100 mg of bovine thyroglobulin. Stir at room temperature for 3 hours and then dialyze against phosphate buffer to remove unbound hapten.

Hapten

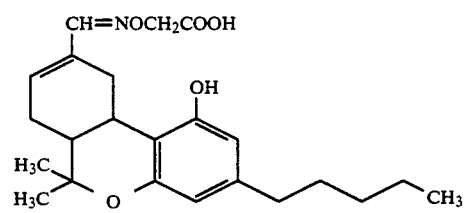

Dissolve 36 mg of ($\Delta^8$-THC-oxime acid compound) in 1.5 ml DMSO. Add 15.5 mg of N-hydroxysuccinimide and 26.5 mg of dicyclohexylcarbodiimide. Stir at room temperature for 2.5 hours. Filter to remove precipitate and add the filtrate to a rapidly stirring solution of 65% DMSO-water (v/v) containing 110 mg of bovine thyroglobulin. Stir at room temperature for 2.5 hours and then dialyze against phosphate buffer to remove unbound hapten.

EXAMPLE 2—PREPARATION OF TRACERS (a) General Procedures for Preparing Tracers 1. DTAF Tracers (GI)

Tracer Derived From DTAF Isomer I

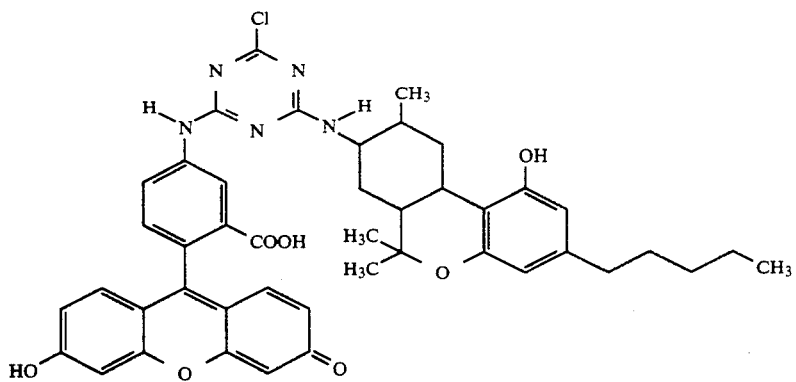

Tracer Derived From DTAF Isomer II

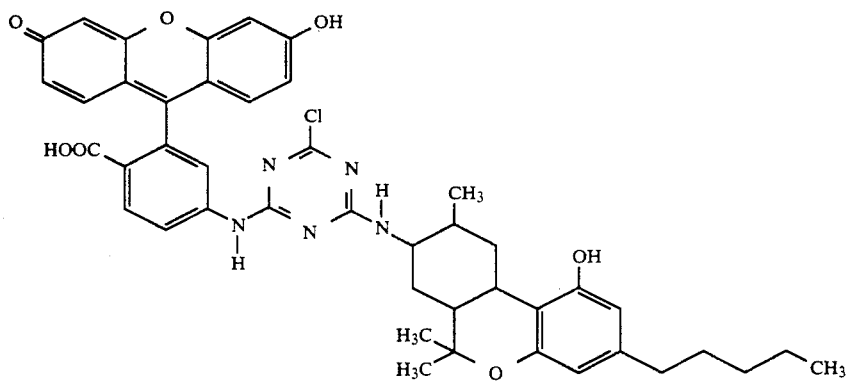

A mixture of the amine (0.01 mmol), DTAF (I or II) (0.01 mmol), triethylamine (2 drops) and methanol (0.1 ml) was stirred at room temperature for 16 hours. The mixture as applied onto a preparative silica gel TLC plate. Development with CHCl$_3$/MeOH (3:1 or 4:1) gave fluorescent bands which were scraped off the plate and eluted with methanol separately. In selected cases, the relatively pure tracer was further purified on a reverse-phase preparative TLC plate (whatman 4803-800, KC-18 F254) using acetonitrile/0.01M phosphate buffer (pH 5.3), (1:1, v/v) as developer.

2. Carboxylfluorescein Tracers (GII)

Tracer Derived From 5-Carboxyfluorescein

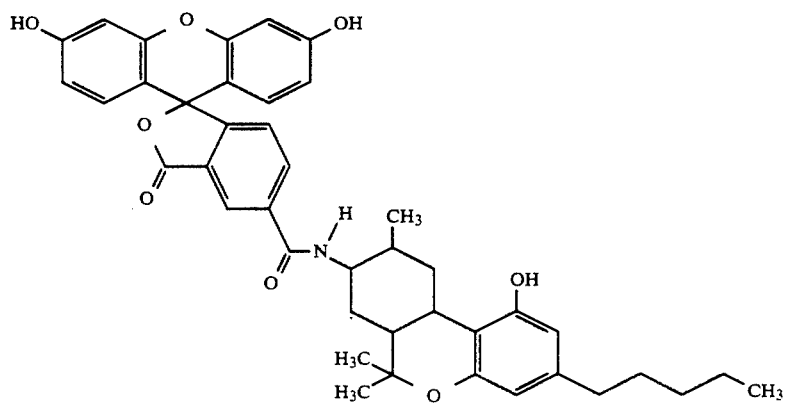

Tracer Derived From 6-Carboxyfluorescein

-continued

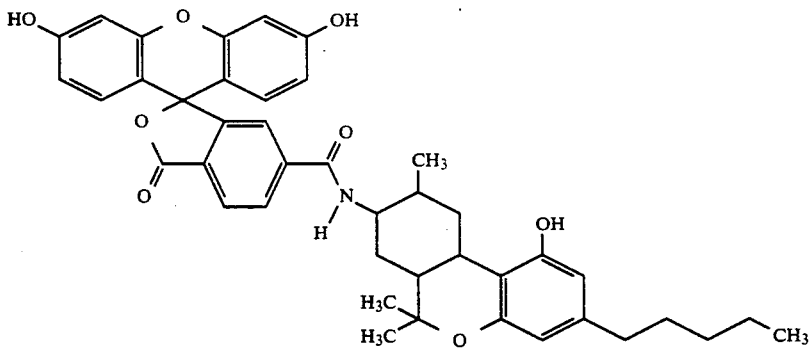

A mixture of the amine (0.01 mmol), fluorescein carboxylic acid (V or VI)-O-succinimide ester (0.01 mmol) and pyridine (0.1 ml) was stirred at room temperature for 16 hours. The mixture was applied to a preparative TLC plate. Development with CHCl3/MeOH (3.1 or 4:1) gave fluorescent bands which were scraped off the plate and eluted with methanol separately.

3. Fluoresceinamine Tracers (GIII)

Tracer Derived From Fluorescein Amine Isomer I

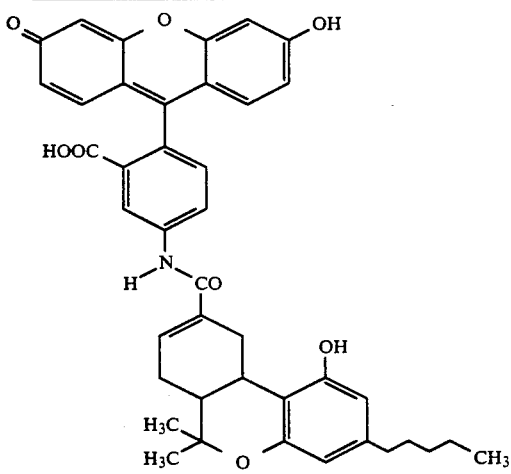

Tracer Derived From Fluorescein Amine Isomer II

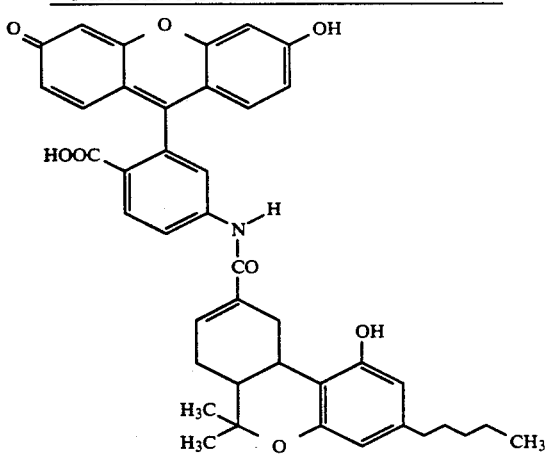

A mixture of the carboxylic acid (0.1 mmol), dicyclohexylcarbodiimide (0.02 mmol) and N-hydroxysuccinimide (0.012 mol) in dry pyridine (0.1 ml) was stirred at room temperature for 1 hour. The active ester formed was then treated with fluoresceinamine (isomer I or II) at the same temperature for 16 hours. The reaction mixture was applied to a preparative silica gel tlc plate (20 cm×20 cm×0.5 mm). Development with CHCl3/MeOH (3:1 or 4:1 depending on the polarity of the substrate) gave fluorescent bands which were scraped off the plate. The individual bands were eluted with methanol and the eluents were collected.

(b) Preparation of Preferred Tracer Precursors
6aR-Trans-1-(acetyloxy)-6a,7,8,9,10,10a-hexahydro-6,6,9-trimethyl-3-pentyl-6H-dibenzo[b,d]pyrano[8.9-b]oxirene To an ice-cold solution of 6aR-trans-1-(acetyloxy)-6a,7,10,10a-tetrahydro-6,6,9-trimethyl-3-pentyl-6H-dibenzo[b.d]pyran(212 mg, 0.59 mmol) in methylene chloride (5 ml) was added with stirring prewashed 80% metachloroperbenzoic acid (157 mg, 0.73 mmol). The reaction mixture was stirred at 0° C. for 1 h and then worked up by partitioning between water and methylene chloride (3 times). The combined organic layers were washed with 10% sodium bicarbonate solution (2 times), water (once), and dried (magnesium sulfate). Rotary evaporation of the solution gave 244 mg of a light yellow liquid.

6aR-Trans-1-(acetyloxy)-6a,7,8,9,10,10a-hexahydro-6,6,9-trimethyl-8-oxo-3-pentyl-6H-dibenzo[b.d.]pyran To a solution of the crude epoxide (64 mg, 0.17 mm) in benzene (2 ml dried over molecular sieve) was added via a syringe 3 drops (30 mg) of boron trifluoride etherate. After the mixture was stirred at room temperature for 5 minutes water was added and the aqueous mixture was extracted with ethyl acetate (2 times). The combined extracts were washed with brine (once), dried (MgSO4) and filtered. Rotary-evaporation of the filtrate gave 60 mg (94% yield) of the desired product.

6aR-Trans-1-(acetyloxy)-8-amino-6a,7,8,9,10,10a-hexahydro-6,6,9-trimethyl-3-pentyl-6H-dibenzo[b.d]pyran A mixture of the ketone obtained above (60 mg, 0.16 mmol) ammonium acetate (123 mg 0.16 mmol) and methanol (2 ml) was stirred at room temperature for 1 hr. Sodium cyanoborohydride was added and the resulting mxiture was stirred at room temperature for 16 h. Water was added and the aqueous mixture was extracted with ethyl acetate (3 times). The combined extracts were washed with brine (one time) and dried (magnesium sulfate). Evaporation of the solution in vacuo gave 62 mg of a crude product which was purified by preparative thin layer chromatography on silica gel. Development with methanol/ammonium hydroxide (99:1) gave 22 mg of a mixture of the title compound and the corresponding deacetylated product (1:1).

6aR-Trans-1-(acetyloxy)-8-amino-6a,7,8,9,10,10a-hexahydro-1-hydroxy-6,6,9-trimethyl-3-pentyl-6H-dibenzo[b,d]pyran The mixture obtained above (22 mg) was stirred with anhydrous potassium carbonate (26 mg, 0.19 mmol) in methanol (0.5 ml) at room temperature for 18 h. Water was added and the aqueous mixture was extracted with ethyl acetate (3 times). The combined extracts were washed with brine (twice) and dried (magnesium suflate) Rotary evaporation of the soution gave a crude product which was further dried in vacuo to give 19 mg of the desired product. (34% yeild two-step from the ketone)

(c) Preparation and Purification of the Most Preferred Tracer

A mixture of the amine (3.3 mg, 0.001 mmol) succinimidyloxy carbonyl fluorescein (vi) (4.3 mg, 0.01 mmol, pyridine (1 drop), and N,N-dimethylformamide (0.1 ml) was stirred at room temperature for 18 h. The mixture was then fractionated by preaprative thin-layer chromatography on a silica gel plate (20 cm×20 cm×0.5 mm). Development with chloroform/methanol (3:1) gave a major fluorescent band (Rf=0.75) which was scraped off the plate and eluted with methanol. Repurification of the tracer was performed as follows: The methanolic solution was rotary-evaporated to dryness and the solid residue was taken up into fresh methanol (1 ml). After applying onto a prepared TLC plate (20 cm×20 cm×0.5 mm), the material was developed with chloroform/methanol (4:1) to give two bands. The amjor band (smaller Rf value) was scraped off the plate and eluted with methanol.

For additional information about the preparation of various derivatives of tetrahydrocannabinol, see Pars et al., "Drugs Derived from Cannabinoids. 1. Nitrogen Analogs, Benzopyranopyridines and Benzopyranopyrroles," Journal of Medical Chemistry Vol. 19, No. 4, 445–545 (1976), the entirety of which is hereby incorporated herein by reference.

EXAMPLE 3

Preparation of Alternative Hapten and Tracer Precursor

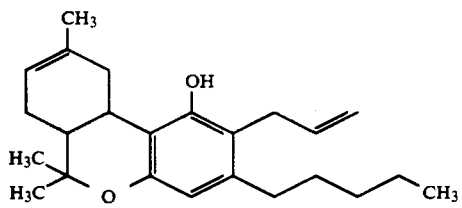

Δ8-THC (1 g) was stirred at reflux with allyl bromide (1 g) in acetone (37.5 ml) in the prsence of K$_2$CO$_3$ (1.7 g) for 18 h. The inorganic salt was filtered off and the filtrate concentrated to give a crude residue (1.05 g) which was then heated with 10 ml of diethylaniline at 200° C. for 3 hr. under nitrogen. The reaction mixture was dissolved in ether and the etherial solution washed successively with dilute hydrochloric acid (3 times), H$_2$O and brine (once each). Evaporation of the dried (MgSO$_4$) solution in vacuo gave a crude material (543 mg).

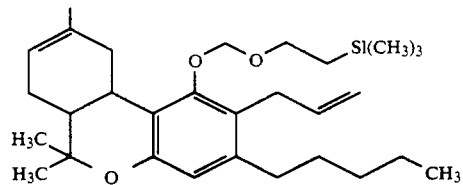

Portion of the crude phenol obtained above (276 mg) was treated at room temperature with 2-(trimethylsilyl) ethoxymethyl chloride (SEM-Cl, 502 mg), and diisopropylethylamine (497 mg) in methylene chloride (4 ml) for 24 hr. The mixture was diluted with ether and the etherial solution was washed with H$_2$O. The washing was reextracted with ether, and the organic layers were combined. Rotary evaporation followed by further drying in vacuo gave 431 mg of the desired product.

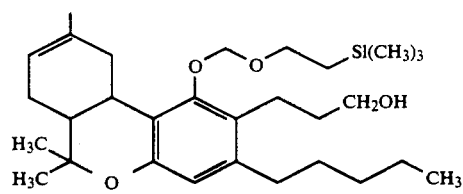

To a solution of the olefin (430 mg) in tetrahydrofuran (7 ml) was added 9-borabicyclo [3.3.1] nonane (9-BBN), 0.5M solution in THF, (6.8 ml). After stirring at room temperature for 18 h, a 3M NaOH solution (14 ml) was added (with slight cooling) followed by 14 ml of 30% H$_2$O$_2$ solution. The aqueous mixture as stirred at 45° for 2 hr. Extractive work-up (ethyl acetate) gave a crude product (1.7 g) which was flash-chromatographed over silica gel. Elution with hexane/ethylacetate (5:1) gave 241 mg of oil.

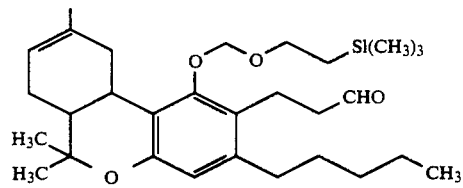

To a solution fo the alcohol (663 mg) in methylene chloride (12 ml) buffered with sodium acetate (66 mg) was added pyridinium chlorochromate (663 mg). After stirring at room temperature, ether was added. The gummy mixture was filtered through a short pad of silica gel and the filtrate was rotary evaporated to give 605 mg of an oil.

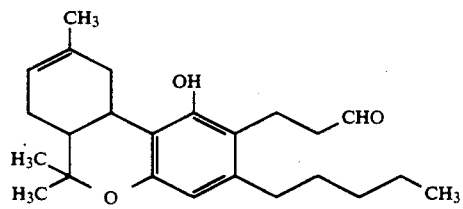

A solution of the trimethylsilyl deriviative (300 mg) in 80% acetic acid was heated at 85° for 15 min. with stirring. The solvent was rotary evaporated and the resulting viscous residue was applied to a flash-column packed with silica gel. Elution with hexane/ethyl acetate (10:1) gave 60 mg of the desired product.

EXAMPLE 4—PREPARATION OF ALTERNATE TRACER (1)

(a) Preparation of Precursor 1,3-Dihydroxy-2-(3-methylbut-2-en-1-yl)-4-pent-1-yl benzene Olivetol (1.49 g) was dissolved in 6.6 ml distilled water and 3.5 ml 88% formnic acid and heated to 80° C. in a water bath. 3-Methyl-3-buten-2-ol (3.5 ml) was added dropwise with stirring over 10 minutes. The reaction was allowed to cool to room temperature and became cloudy. The reaction was poured into 50 ml distilled water and extracted with methylene chloride. The methylene chloride was removed in vacuo. The residue was chromatographed on silica gel eluting with chloroform. The appropriate fractions were combined (TLC Rf. 0.9, 1:4 ethyl acetate: petroleum ether) to yield 0.252 g of pure product.

3,6-Diiodo-2,2-dimethyl-5-hydroxy-7-pent-1-yl chromane 1,3-Dihydroxy-2-(3-methylbut-2-en-1-yl)-y-pent-1-yl benzene (0.497 g) was dissolved in 5 ml methylene chloride and N-iodosuccinimide (0.902 g) was added with stirring at room temperature under a nitrogen atmosphere. The reaction was stirred for 28 hours and then chromatographed on a silica gel column eluting with a chloroform/hexane mixture. (TLC Rf=0.6, 1:4 chloroform:hexane). The appropriate fractions were combined to yield 0.293 g of pure product.

3-Cyano-2,2-dimethyl-5-hydroxy-6-iodo-7pent-1-yl-chromane 3,6-Diiodo-2,2-dimethyl-5-hydroxy-7-pent-1-yl chromane (0.293 g) and potassium cyanide (50 mg) were dissolved in 15 ml absolute ethanol and heated to reflux. After 4.5 hours, the reaction was allowed to cool to room temperature. The solvent was removed in vacuo. Water was added and extracted with methylene chloride. The methylene chloride was removed in vacuo. The residue was chromatographed on a silica gel column eluted with chloroform (TLC Rf=0.2, chloroform). The appropriate fractions were combined to yield 51 mg of product.

3-(Aminomethyl)-2,2-dimethyl-5-hydroxy-7-pent-1-yl chromane 3-cyano-2-dimethyl-5-hydroxy-6-iodo-7-pent-1-yl chromane (51 mg) and lithium aluminum hydride (45 gm) were dissolved in 22 ml dry tetrahydrofuran under a nitrogen atmosphere and heated to reflux. After 1 day, the rection was allowed to cool to room temperature. Added 1 ml distilled water dropwise and then added 20 ml more. The water was extraced with ethyl ether. The ether layer was dried (MgSO4) and removed in vacuo. A brown oil (38 mg) was obtained and was a single spot on a silica gel TLC (Rf.=0.8, 2:6:0.1 methanol:-chloroform:ammonium hydroxide)

(b) Preparation of Tracer

3-[(fluorescein-6-yl carbonyl)aminomethyl]-2,2-dimethyl-5-hydroxy-7-pent-1-yl chromane chromane 3-(aminomethyl)-2,2-dimethyl-5-hydroxdy-7-pent-yl chromane (5 mg) was added to a 1 ml pyridine solution containing 6-carboxyfluorescein (7 mg), dicyclohexyl-carbodiimide (7 mg) and N-hydroxy succinimide (3 mg). After 16 hours of stirring in a stoppered flask at room temperature, the product was isolated on silica/-gel preparative plates by elution with the appropriate mixture of methanol and chloroform [TLC Rf-0.7, 1:3 in ethanol:chloroform].

EXAMPLE 4a

Preparation of Alternate Tracer (2)
5,5-Dimethyl-8-(1,2-dimethylhepytyl)-10-hydroxy-2-(fluorescein-6-ylcarbonyl-5H-[1]benzopyrano[3,4-d]piperidine 5,5-Dimethyl-8-(1,2-dimethylheptyl)-10-hydroxy-5H-[1]benzopyrano-[3,4-d]piperidine (5 mg) [prepared by the method of Pars et al., *J. Med. Chem.* 1976, 19, 445] was added to a 1.5 ml pyridine solution containing 6-carboxyfluorescein (6 mg), dicyclohexylcarbodiimide (6 mg) and N-hydroxysuccinimide (2 mg). After 2 days of stirring in a stoppered flask at room temperature, the product was isolated on silica gel preparative plates by elution with the appropriate mixture of methanol and chloroform [TLC Rf=0.3, 1:4 methanol:chloroform].

EXAMPLE 4A

Preparation of Alternate Tracer

Preparation of 5,5-Dimethyl-8-pentyl-10-hydroxy-2-(fluorescein-6-ylcarbonyl)-5H-[1]benzopyrano[3,4-d]piperidine

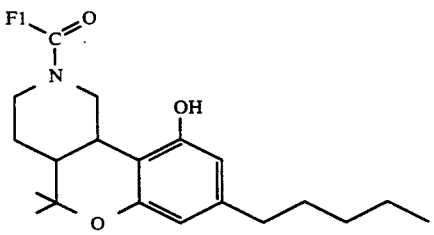

5,5-Dimethyl-8-pentyl-10-hydroxy-2-(fluorescein-6-yl-carbonyl)-5H-[benzopyrano[3,4-d]piperidine is prepred using the procedure described in Example 4.

EXAMPLE 5

THC Assay

A. Reagents

All precentages expressed herein are weight/volume unless otherwise indicated.

(1) pretreatment Solution—0.1 MTris Buffer pH 7.5; 10 mg/ml riboflavin binding protein; 0.1% sodium azide.
(2) Tracer: Consisting of 111 nanomolar of the compound of formula IV in 5% cholic acid buffer at pH 7.5, and 0.1% sodium azide.
(3) Antibody: Sheep antiserum consisting of antiserum raised against preferred immunogen appropriately diluted in 0.1M Tris buffer pH 7.5: 0.1% sodium azide and 2% ethylene glycol, 0.5% bovine gamma globulin.

(4) Diluent buffer: 0.1 sodium phosphate, pH 7.5, 0.01% bovine gamma globulin and 0.1% sodium azide.

(5) Calibrators; 11-nor-delta-8-tetrahydrocannabinol-9-carboxylic acid or 11-nor-delta-9-tetrahydrocannabinol-9-carboxylic acid in normal human urine (containing 5% DMSO, 0.5% BSA and 0.9% NaCl) at concentrations of 0.0, 25, 40, 60, 80 and 200 micrograms per liter for 11-nor-delta-8-tetrahydrocannabinol-9-carboxylic acid preserved with 0.1% sodium azide, and 0.0, 25, 40, 60, 80 and 135 micrograms per liter for 11-nor-delta-9-tetrahydrocannabinol-9-carboxylic acid preserved with 0.1% sodium azide.

(6) Controls: 11-nor-delta-8-tetrahydrocannabinol-9-carboxylic acid or 11-nor-delta-9-tetrahydrocannabinol-9-carboxylic acid in normal human urine (containing 5% DMSO, 0.5% BSA and 0.9% NaCl) at concentrations of 35, 50 and 120 micrograms per liter for 11-nor-delta-8-tetrahydrocannabinol-9-carboxylic acid preserved with 0.1% sodium azide, and 35, 50 and 110 micrograms per liter for 11-nor-delta-9-tetrahydrocannabinol-9-carboxylic acid preserved with 0.1% sodium azide.

(7) Wash: A solution containing about 50% dimethylsulfoxide and 0.45% sodium chloride.

All polarized fluorescence measurements were made using the Abbott TDx ® Analyzer.

B. Assay Protocol

Fifty (50) microliters of urine, serum or plasma are required. The calibrators, controls, or unknown samples are pipetted directly into the sample well of the TDx ® sample cfartridge. One of the advantages of this procedure is that the sample does not require any special preparation. The sample is placed directly into a sample carousel, the caps from each of the four reagent containers in the kit are removed and placed into designated well inside the TDx ® analyzer, and the assay procedure from this point is fully automated.

(1) 5 ul of unknown sample, one half of the pretreatment solution and all of the antiserum is added to the cuvette. Sufficient diluent is added to raise the volume to 1.0 ml.

(2) A background intensity reading is taken.

(3) The remainder of the sample, and pretreatment solution plus 25 ul of the tracer solution is added to the cuvette. Sufficient diluent is added to raise the volume to 2.0 ml.

(4) The fluorescence polarization due to tracer binding to the antibody is obtained by substracting the polarized fluorescence intensities of the background from the final polarized fluorescence intensities of the mixture.

(5) The polarization values obtained are inversely proportional to the THC concentration of each sample.

(6) The polarization value for a sample is compared to a standard curve prepared using calibrators of known THC content.

With respect to the foregoing preferred procedure, it should be noted that the tracer, antibody, pretreatment solution, calibrators and controls should be stored between about 2° and about 8° C., while the dilution buffer should be stored at ambient temperature. A standard curve and controls should be run every two weeks, with each calibrator and control run in duplicate. Controls should be run daily and all samples can be run in replicates if so desired.

EXAMPLE 6—WASH SOLUTION

Various wash solutions were evaluated for ability to minimize cannabinoid adhesion to the probe of the TDx ® analzyer. Carryover was determined as follows: on a TDx ® carousel, positions 1 to 5 were samples of A calibrator, which by definition contains 0.0 mg/ml of THC. Positions 6–15 were samples of urine which contained 10 ug/ml of $\Delta^8$-THC-9-carboxylic acid. Positions 16–20 again contained A calibrator. Carryover was determined by the concentration of drug measured in position 16 divided by 10 ug/ml. Acceptable carryover was defined as less than 0.05%. Results are reported in Table 1 below.

TABLE 1

| Diluent used | Carryover |
| --- | --- |
| TDx buffer (state composition) | unacceptable |
| TDx wash pack (state composition) | unacceptable |
| 63% 1-butanol, 20% DMSO | unacceptable |
| 25% 1-propanol, 50% DMSO | unacceptable |
| 25% methanol, 50% DMSO | unacceptable |
| 50% methanol | unacceptable |
| 5% cholate, 20% 1-propanol, 50% DMSO | unacceptable |
| 5% SDS, 50% DMSO | unacceptable |
| 15% 5-SSA, 50% DMSO | unacceptable |
| 10% Tetraethylammonium hydroxide | unacceptable |
| 4% Triton X-152, 30% 1-propanol, 50% DMSO | unacceptable |
| 4% Triton GR-5M, 20% 1-propanol, 50% DMSO | unacceptable |
| 4% Triton X-165, 20% 1-propanol, 50% DMSO | unacceptable |
| 4% Triton N-101, 20% 1-propanol, 50% DMSO | unacceptable |
| 1% Lithium diiodosalicylate, 20% 1-propanol, 50% DMSO | unacceptable |
| 50% DMSO, 045% saline | acceptable |

What is claimed is:

1. A tracer comprising the structure:

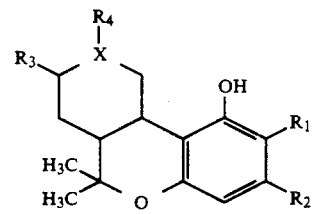

wherein:

$R_1$ is H when $R_2$ is n-pentyl, $R_3$ is H, $R_4$ is RZQ, and X is =C—, —C= or —CH; or $R_1$ is H when $R_2$ is n-pentyl, $R_3$ is RZQ, $R_4$ is CH$_3$ and X is =C—, —C= or —CH; or $R_1$ is RZQ when $R_2$ is n-pentyl, $R_3$ is H, $R_4$ is CH$_3$ or COOH, and X is =C—, —C= or —CH; or $R_1$ is H when $R_2$ is —CH$_2$RZQ, $R_3$ is H, $R_4$ is CH$_3$ or COOH, and X is =C—, —C= or —CH; or $R_1$ is H when $R_2$ is $R_5$, $R_3$ is H, $R_4$ is H or RZQ, and X is —N—;

$R_5$ is an alkyl group of from about 5 to about 9 carbon atoms;

R is a linking group consisting of from about 0 to about 15 carbon atoms and heteroatoms, wherein said heteroatoms are N, O, S, Cl, Br, I or F;

Z is C=O, C=NH, NH, or SO$_2$; and

Q is fluorescein or a derivative of fluorescein, said fluorescein or derivative of fluorescein providing said tracer with the ability to emit fluorescence.

2. The tracer of claim 1 wherein ZQ is fluorescein-5-yl carbonyl.

3. The tracer of claim 1 wherein ZQ is fluorescein-6-yl carbonyl.

4. The tracer of claim 1 wherein ZQ is fluorescein-5-yl amino.

5. The tracer of claim 1 wherein ZQ is fluorescein-6-yl amino.

6. A tracer compound for use in a fluorescence polarization assay for determining the presence or amount of tetrahydrocannabinoids and tetrahydrocannabinoid metabolites in a test sample of biological fluid comprising the structure:

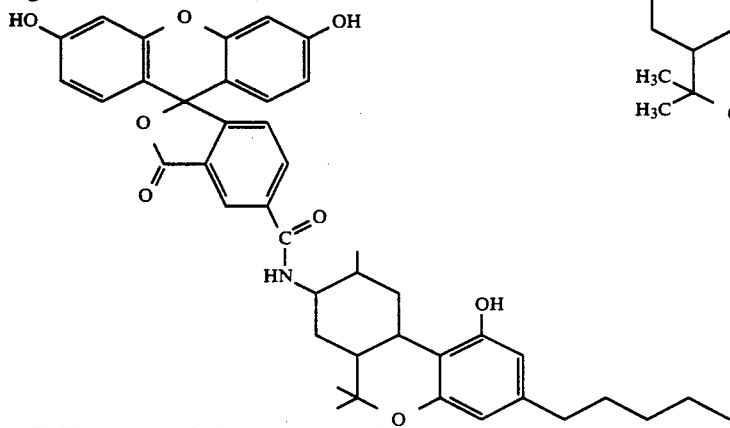

7. The tracer of claim 1 wherein ZQ is an imino, an iminocarbonyl, a carbonyl, a carbonimidoyl, an iminosulfonyl, a sulfonyl, an iminocarbonimidoyl, a thiocarbonyldiimino, an iminocarbonyloxy, an iminothiocarbonyloxy, a (sulfonyliminocarbonyl) diimino or a triazinyldiimino derivative of fluorescein, said derivative of fluorescein being linked to R by said imino, iminocarbonyl, carbonyl, carbonimidoyl, iminosulfonyl, sulfonyl, iminocarbonimidoyl, thiocarbonyldiimino, iminocarbonyloxy, iminothiocarbonyloxy, (sulfonyliminocarbonyl) diimino or triazinyldiimino group.

8. The tracer of claim 1 wherein $R_1$ is H, $R_2$ is n-pentyl, $R_3$ is RZQ, $R_4$ is $CH_3$ and X is =C—.

9. The tracer of claim 1 wherein Q is carboxyfluorescein.

10. The tracer of claim 8 wherein Q is carboxyfluorescein.

11. A tracer comprising the structure:

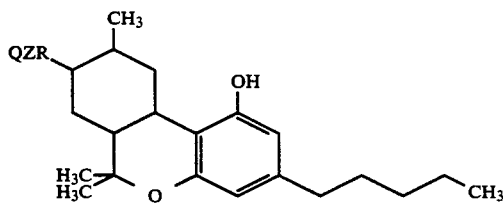

wherein:
R is a linking group consisting of from about 0 to about 15 carbon atoms and heteroatoms, wherein said heteroatoms are N, O, S, Cl, Br, I or F;
Z is C=O, C=NH, NH, or $SO_2$; and
Q is fluorescein or a derivative of fluorescein, said fluorescein or derivative of fluorescein providing said tracer with the ability to emit fluorescence.

12. The tracer of claim 11 wherein ZQ is an imino, an iminocarbonyl, a carbonyl, a carbonimidoyl, an iminosulfonyl, a sulfonyl, an iminocarbonimidoyl, a thiocarbonyldiimino, an iminocarbonyloxy, an iminothiocarbonyloxy, a (sulfonyliminocarbonyl) diimino or a triazinyldiimino derivative of fluorescein, said derivative of fluorescein being linked to R by said imino, iminocarbonyl, carbonyl, carbonimidoyl, iminosulfonyl, sulfonyl, iminocarbonimidoyl, thiocarbonyldiimino, iminocarbonyloxy, iminothiocarbonyloxy, (sulfonyliminocarbonyl) diimino or triazinyldiimino group.

13. A tracer comprising the structure:

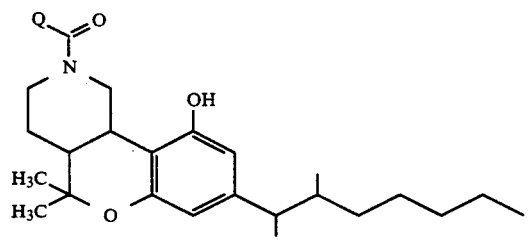

wherein Q is fluorescein or a derivative of fluorescein, said fluorescein or derivative of fluorescein providing said tracer with the ability to emit fluorescence.

14. A tracer comprising the structure:

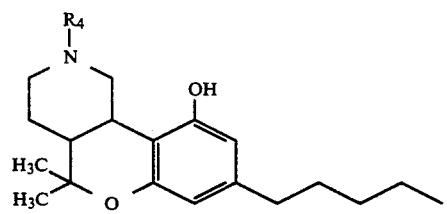

wherein:
$R_4$ is RZQ;
R is a linking group consisting of from about 0 to about 15 carbon atoms and heteroatoms, wherein said heteroatoms are N, O, S, Cl, Br, I or F;
Z is C=O, C=NH, $SO_2$, NH, $NCH_3$ or $CH_2$; and
Q is a fluorescein or a derivative of fluorescein, said fluorescein or derivative of fluorescein providing said tracer with the ability to emit fluorescence; wherein ZQ is an imino, an iminocarbonyl, an iminosulfonyl, a thiocarbonyldiimino, or a (sulfonyliminocarbonyl) diimino derivative of fluorescein, said derivative of fluorescein being linked to R by said imino, iminocarbonyl, iminosulfonyl, thiocarbonyldiimino or (sulfonyliminocarbonyl) diimino group.

* * * * *